(12) United States Patent
White et al.

(10) Patent No.: US 6,869,439 B2
(45) Date of Patent: Mar. 22, 2005

(54) ULTRASONIC DISSECTOR

(75) Inventors: Jeffrey S. White, Ridgefield, CT (US);
Howard Alliger, Melville, NY (US);
Ronald R. Manna, Valley Stream, NY
(US); Daniel Voic, Clifton, NJ (US)

(73) Assignees: United States Surgical Corporation,
Norwalk, CT (US); Misonix, Inc.,
Farmingdale, NY (US)

( * ) Notice: Subject to any disclaimer, the term of this patent is extended or adjusted under 35 U.S.C. 154(b) by 0 days.

(21) Appl. No.: 10/223,150

(22) Filed: Aug. 19, 2002

(65) Prior Publication Data

US 2002/0198555 A1 Dec. 26, 2002

Related U.S. Application Data

(63) Continuation of application No. 09/457,951, filed on Dec. 9, 1999, now abandoned, which is a continuation of application No. 08/925,184, filed on Sep. 8, 1997, now abandoned.
(60) Provisional application No. 60/026,336, filed on Sep. 19, 1996.

(51) Int. Cl.[7] .............................................. A61B 17/32
(52) U.S. Cl. ..................... 606/169; 606/170; 606/171
(58) Field of Search ................................. 606/167, 168, 606/169, 170, 171

(56) References Cited

U.S. PATENT DOCUMENTS

| 2,002,594 A | 5/1935 | Wappler et al. |
| 2,011,169 A | 8/1935 | Wappler |
| 2,714,890 A | 8/1955 | Vang |

(List continued on next page.)

FOREIGN PATENT DOCUMENTS

| DE | 2 032 501 A | 1/1972 |
| EP | 0 394 583 A2 | 10/1990 |
| EP | 0 456 470 A1 | 11/1991 |
| JP | 61-181630 A2 | 8/1986 |
| JP | 1-167802 A2 | 7/1989 |
| JP | 1-232948 A2 | 9/1989 |
| JP | 1-232949 A2 | 9/1989 |
| JP | 8-275948 | 10/1996 |
| JP | 8-275949 | 10/1996 |
| JP | 8-275951 | 10/1996 |
| JP | 9-98980 | 4/1997 |
| SU | 1155256 A1 | 5/1985 |
| WO | WO 86/02257 A1 | 4/1986 |
| WO | WO 94/20025 A1 | 9/1994 |
| WO | WO 98/06446 | 2/1998 |

OTHER PUBLICATIONS

UltraCision Incorporated, Harmonic Scalpel Operating Manual, Ref. N Mar. 1995, 53 pages.
UltraCision Incorporated, Harmonic Scalpel Price List, Jul. 1995, 7 pages.
UltraCision Incorporated, The Harmonic Scalpel for Gynecological Surgery, 1993, 4 pages.
Ultracision CS/LS Layout, Jul. 24, 1995, 2 pages.
Snowden–Spencer, Inc., Endoscopic Plastic Surgery, 1993, 10 pages.

Primary Examiner—Michael J. Milano
Assistant Examiner—Charles H. Sam

(57) ABSTRACT

An ultrasonic surgical instrument for dissection and coagulation of tissue is provided. The surgical instrument includes a vibration coupler supported within a housing and operably connected to an ultrasonic generator. An angled blade member is connected to the distal end of the vibration coupler to conduct high frequency vibration from the ultrasonic generator to the blade member. A clamp member is positioned adjacent to the blade member and is movable from a first position to a second approximated position. The clamp member and angled blade member combine to enhance contact between the tissue and the blade member during operation of the instrument to improve the performance of the instrument.

23 Claims, 6 Drawing Sheets

U.S. PATENT DOCUMENTS

| | | | |
|---|---|---|---|
| 2,874,470 A | | 2/1959 | Richards |
| 3,086,288 A | | 4/1963 | Balamuth et al. |
| 3,427,480 A | | 2/1969 | Robinson |
| 3,483,918 A | | 12/1969 | Wognum |
| 3,526,219 A | | 9/1970 | Balamuth |
| 3,636,943 A | | 1/1972 | Balamuth |
| 3,752,161 A | | 8/1973 | Bent |
| 3,792,701 A | | 2/1974 | Kloz et al. |
| 3,862,630 A | * | 1/1975 | Balamuth |
| 3,899,829 A | | 8/1975 | Storm et al. |
| 3,930,173 A | | 12/1975 | Banko |
| 4,428,748 A | | 1/1984 | Peyman et al. |
| 4,522,206 A | | 6/1985 | Whipple et al. |
| 4,669,453 A | | 6/1987 | Atkinson et al. |
| 4,672,965 A | | 6/1987 | Baum |
| 4,682,597 A | | 7/1987 | Myers |
| 4,733,662 A | * | 3/1988 | DeSatnick et al. ........... 128/305 |
| 4,887,612 A | * | 12/1989 | Esser et al. ................. 128/751 |
| 4,907,591 A | | 3/1990 | Vasconcellos et al. |
| 5,026,387 A | | 6/1991 | Thomas |
| 5,047,043 A | | 9/1991 | Kubota et al. |
| 5,057,098 A | | 10/1991 | Zelman |
| 5,057,119 A | | 10/1991 | Clark et al. |
| 5,059,210 A | | 10/1991 | Clark et al. |
| 5,062,827 A | * | 11/1991 | Wiksell ....................... 604/22 |
| 5,122,993 A | | 6/1992 | Hikita et al. |
| 5,147,357 A | * | 9/1992 | Rose et al. ................... 606/49 |
| 5,167,725 A | | 12/1992 | Clark et al. |
| 5,176,677 A | | 1/1993 | Wuchinich |
| 5,180,363 A | | 1/1993 | Idemoto et al. |
| 5,188,102 A | | 2/1993 | Idemoto et al. |
| 5,190,541 A | | 3/1993 | Abele et al. |
| 5,201,759 A | | 4/1993 | Ferzli |
| 5,202,066 A | | 4/1993 | Furusawa et al. |
| 5,217,460 A | * | 6/1993 | Knoepfler .................... 606/52 |
| 5,222,937 A | | 6/1993 | Kagawa |
| 5,254,082 A | | 10/1993 | Takase |
| 5,263,957 A | | 11/1993 | Davison |
| 5,267,998 A | | 12/1993 | Hagen |
| 5,322,055 A | * | 6/1994 | Davison et al. ............... 601/2 |
| 5,334,183 A | | 8/1994 | Wuchinich |
| 5,342,380 A | | 8/1994 | Hood |
| 5,346,502 A | | 9/1994 | Estabrook et al. |
| 5,352,222 A | | 10/1994 | Rydell |
| 5,383,883 A | | 1/1995 | Wilk et al. |
| 5,389,104 A | | 2/1995 | Hahnen et al. |
| 5,391,144 A | | 2/1995 | Sakurai et al. |
| 5,393,207 A | | 2/1995 | Maher et al. |
| 5,422,049 A | | 6/1995 | Kruger et al. |
| 5,431,674 A | * | 7/1995 | Basile et al. ................. 606/170 |
| 5,441,512 A | | 8/1995 | Muller |
| 5,484,402 A | | 1/1996 | Saravia et al. |
| 5,527,313 A | * | 6/1996 | Scott et al. ................... 606/51 |
| 5,562,693 A | | 10/1996 | Devlin et al. |
| 5,679,248 A | | 10/1997 | Blaney |
| 5,776,155 A | | 7/1998 | Beaupre et al. |
| 5,800,448 A | | 9/1998 | Banko |
| 5,807,313 A | | 9/1998 | Delk et al. |
| 5,810,859 A | | 9/1998 | DiMatteo et al. |
| 5,873,873 A | | 2/1999 | Smith et al. |
| 5,906,628 A | | 5/1999 | Miyawaki et al. |
| 5,919,206 A | | 7/1999 | Gengler et al. |
| 5,922,001 A | | 7/1999 | Yoon |
| 5,944,737 A | | 8/1999 | Tsonton et al. |
| 5,954,746 A | | 9/1999 | Holthaus et al. |
| 5,955,035 A | | 9/1999 | Dinzburg et al. |
| 5,980,510 A | | 11/1999 | Tsonton et al. |
| 6,004,335 A | | 12/1999 | Vaitekunas et al. |
| 6,024,750 A | | 2/2000 | Mastri et al. |
| 6,036,667 A | | 3/2000 | Manna et al. |
| 6,053,906 A | | 4/2000 | Honda et al. |
| 6,056,735 A | | 5/2000 | Okada et al. |
| 6,063,050 A | | 5/2000 | Manna et al. |
| 6,063,098 A | | 5/2000 | Houser et al. |
| 6,068,647 A | | 5/2000 | Witt et al. |
| 6,095,772 A | | 8/2000 | Ramey et al. |
| 6,096,033 A | | 8/2000 | Tu et al. |
| 6,129,735 A | | 10/2000 | Okada et al. |
| 6,162,194 A | | 12/2000 | Shipp |
| 6,280,407 B1 | | 8/2001 | Manna et al. |
| 6,340,352 B1 | | 1/2002 | Okada et al. |
| 6,358,264 B2 | | 3/2002 | Banko |
| 6,468,286 B2 | | 10/2002 | Mastri et al. |

* cited by examiner

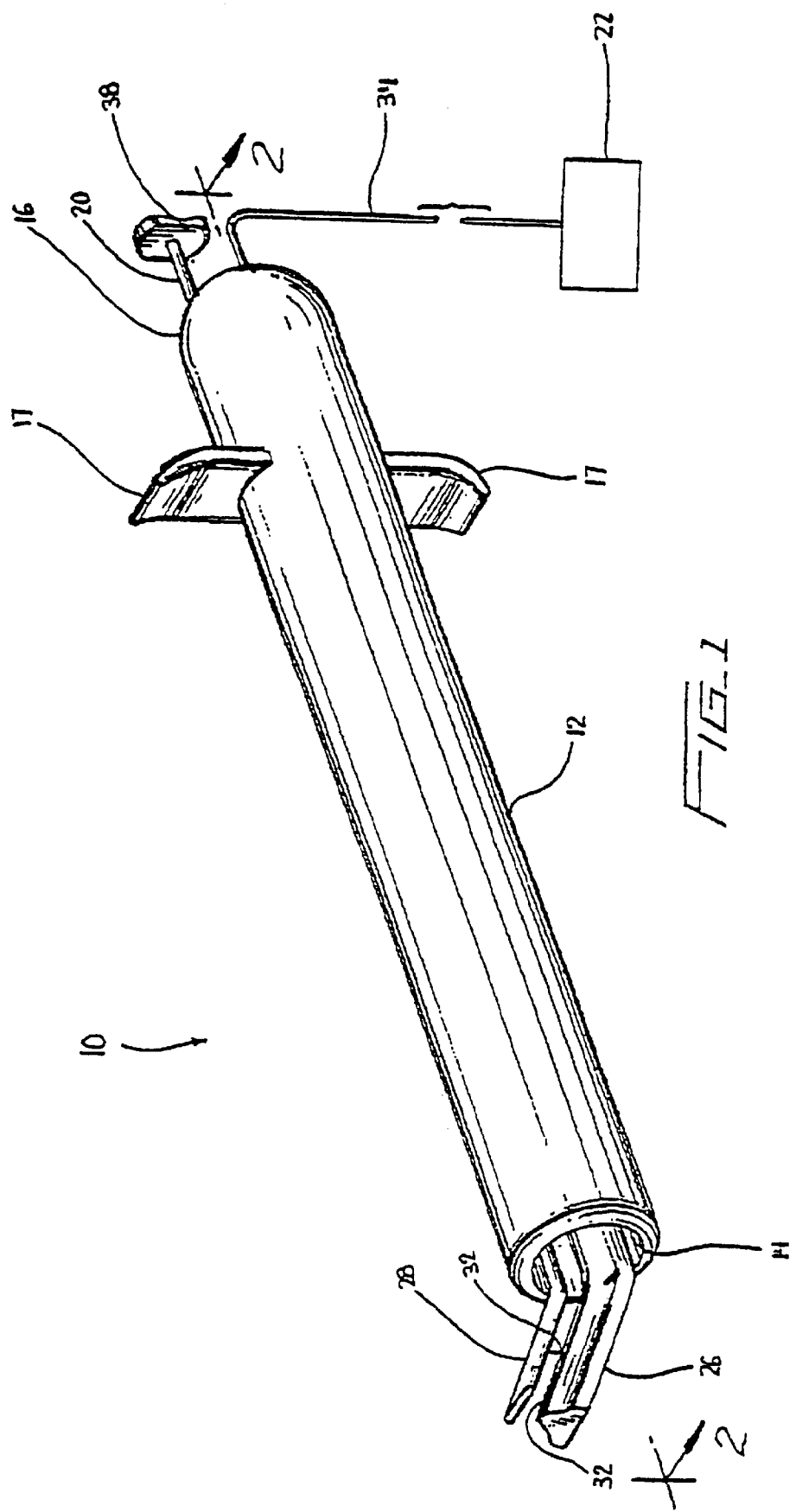

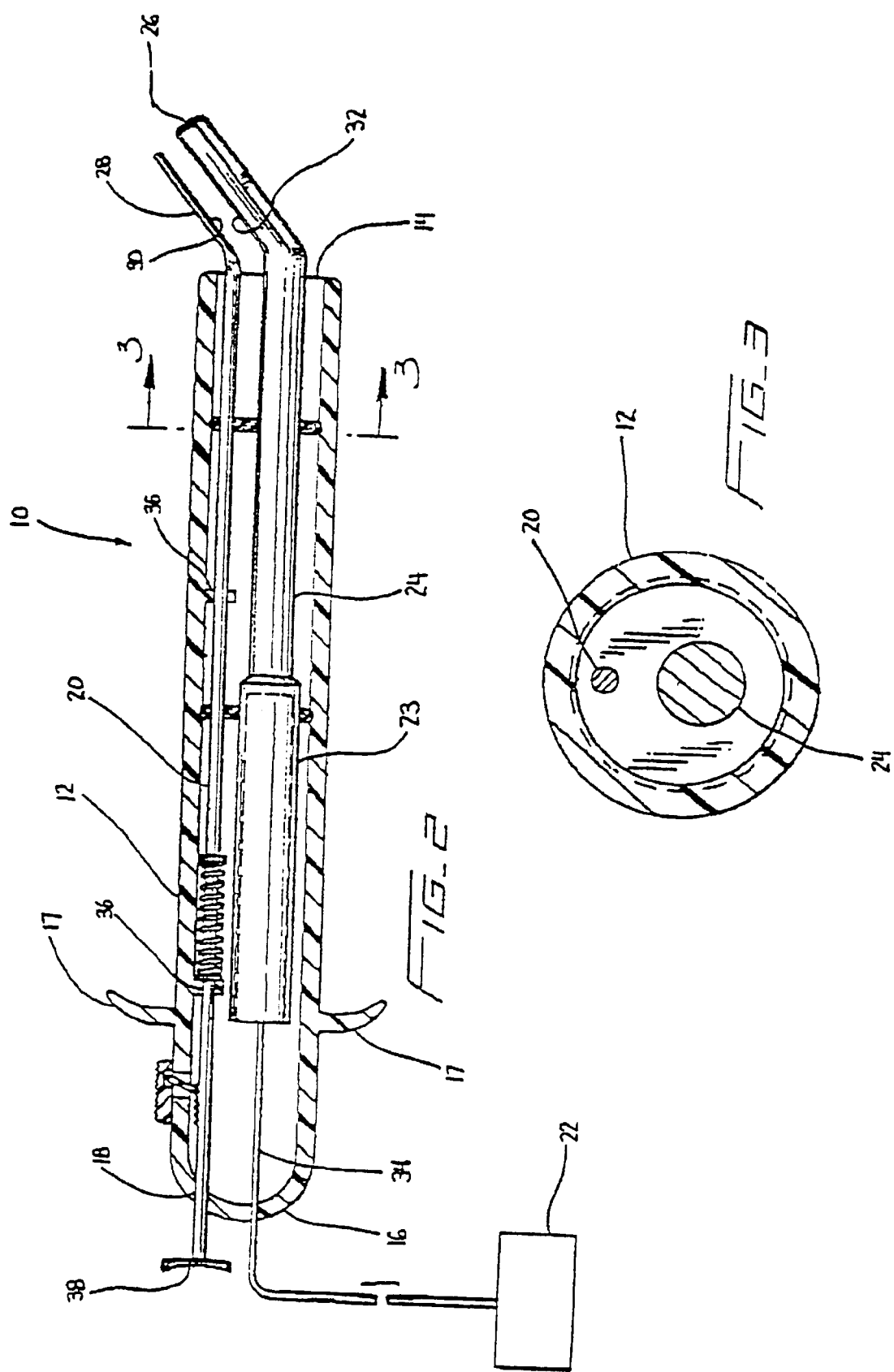

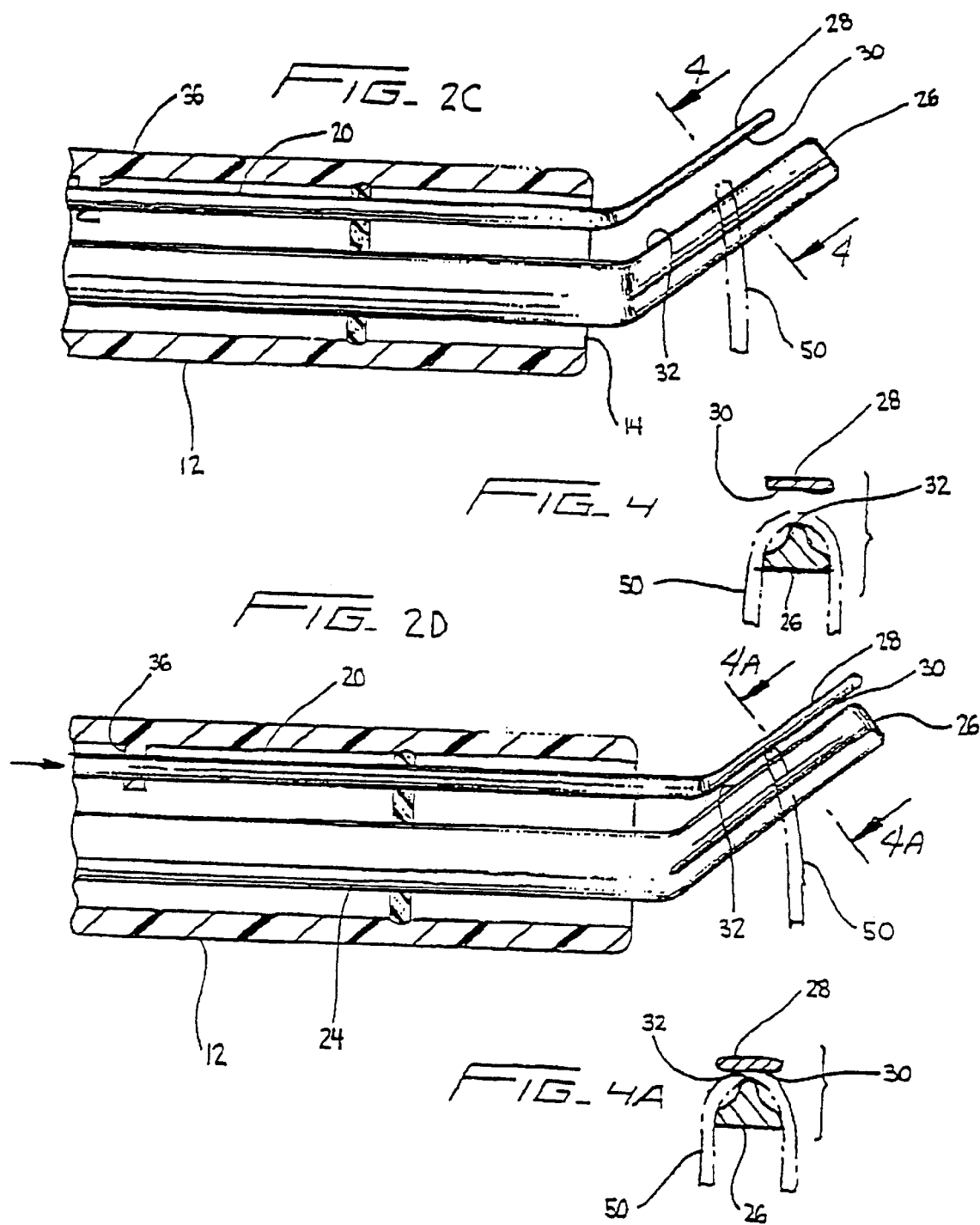

ULTRASONIC DISSECTOR

This application is a continuation and claims priority from U.S. application Ser. No. 09/457,951, filed Dec. 9, 1999, now abandoned, which is a continuation and claims priority from U.S. application Ser. No. 08/925,184 filed Sep. 8, 1997, now abandoned, which claims priority from provisional application Ser. No. 60/026,336 filed Sep. 19, 1996, each of which are incorporated in their entirety herein by reference.

BACKGROUND

1. Technical Field

The present disclosure relates to an ultrasonic instrument for surgical use. More specifically, the present disclosure relates to an ultrasonic instrument having an angled blade member and a clamp member particularly suited for use in performing dissection and coagulation of tissue.

2. Background of Related Art

Ultrasonic instruments for surgical use and the benefits associated therewith are well known. For example, the use of an ultrasonic generator in conjunction with a surgical scalpel facilitates faster and easier cutting of organic tissue and accelerates blood vessel clotting in the area of the cut, i.e., accelerated coagulation. Improved cutting results from increased body tissue to scalpel contact caused by the high frequency of vibration of the scalpel blade with respect to body tissue. Improved coagulation results from heat generated by contact between the scalpel blade and the body tissue as the scalpel blade is vibrated at a high frequency. Thus, in order to reap the advantages associated with ultrasonic energy, good blade to tissue contact is important.

U.S. Pat. No. 3,862,630 ("Balamuth") discloses an ultrasonic system including an ultrasonic motor, a tool member having a working surface oriented normal to the direction of mechanical vibration generated by the ultrasonic motor, and a clamp member extending parallel to the tool member for compressing tissue against the tool member. U.S. Pat. No. 5,322,055 ("Davison") discloses an ultrasonic surgical instrument adapted for endoscopic use having a blade and a clamp movable in relation to the blade to capture tissue therebetween. The blade and the clamp define a clamping region having a plane which is parallel to the longitudinal axis of the surgical instrument. During an endoscopic procedure, movement of the instrument is limited to movement along an axis parallel to the plane of the clamping region. Thus, no additional blade force is imposed on the body tissue as a result of movement of the instrument.

Accordingly, a need exists for an improved ultrasonic surgical instrument which is easy to use and provides fast and easy cutting and improved coagulation.

SUMMARY

In accordance with the present disclosure, an ultrasonic surgical instrument is provided for dissection and coagulation of tissue. The surgical instrument includes a housing and a vibration coupler supported within the housing operably connected to an ultrasonic generator. An angled blade member is connected to the distal end of the vibration coupler to conduct high frequency vibration to the blade member. A clamp member may be positioned adjacent to the blade member and is movable from a first position to a second approximated position to capture tissue therebetween. The clamp member and angled blade member combine to enhance contact between the tissue and the blade member during operation of the instrument to improve the performance of the instrument.

BRIEF DESCRIPTION OF THE DRAWINGS

Various preferred embodiments are described herein with reference to the drawings, wherein:

FIG. 1 is a perspective view of one embodiment of the ultrasonic instrument;

FIG. 2 is a side partial cross-sectional view of the ultrasonic instrument shown in FIG. 1;

FIG. 2C is a side partial cross-sectional view of the clamp member and blade member of the ultrasonic instrument shown in FIG. 1 in the open position;

FIG. 2D is a side partial cross-sectional view of the clamp member and the blade member of the ultrasonic instrument shown in FIG. 1 in the closed position;

FIG. 3 is a cross-sectional view taken along section line 3—3 of FIG. 2;

FIG. 4 is a cross-sectional view taken along section line 4—4 of FIG. 2C;

FIG. 4A is a cross-sectional view taken along section line 4A—4A of FIG. 2D;

DETAILED DESCRIPTION OF THE PREFERRED EMBODIMENTS

Figure 2B:
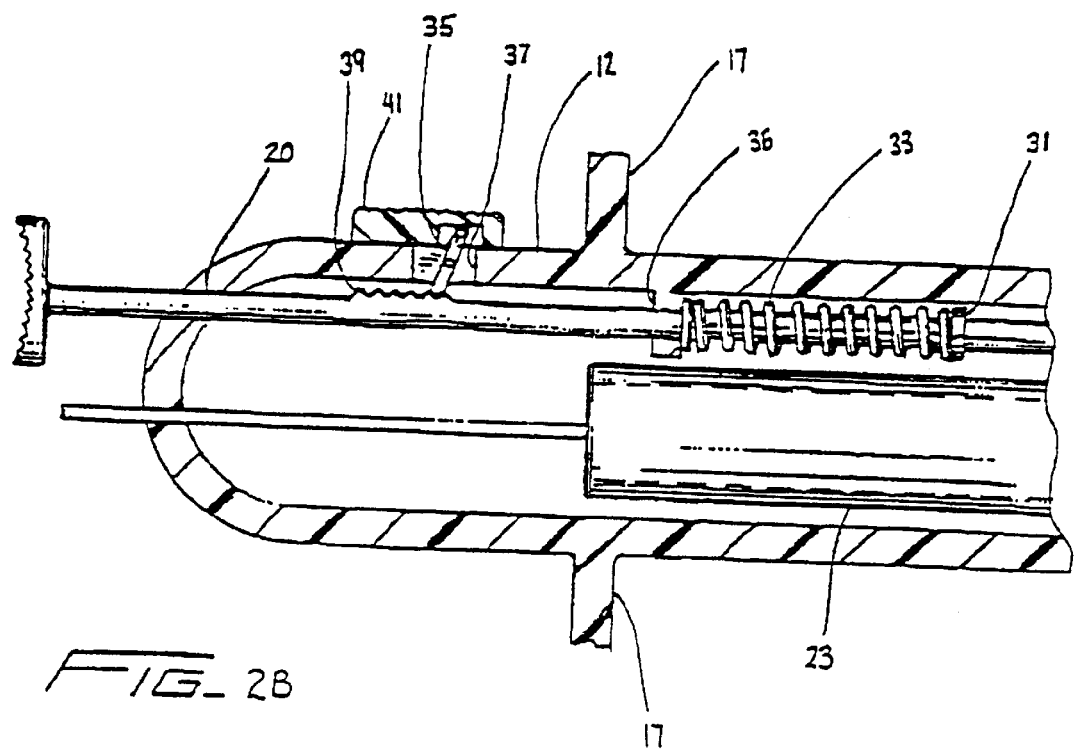
FIG. 2B is a side partial cross-sectional view of the proximal end of the ultrasonic instrument shown in FIG. 1 further including a biasing and retaining mechanism wherein the actuation rod is retained in a retracted position.

Preferred embodiments of the presently disclosed ultrasonic dissector will now be described in detail with reference to the drawings, in which like reference numerals designate identical or corresponding elements in each of the several views.

FIGS. 1–3 illustrate one embodiment of the presently disclosed ultrasonic instrument shown generally as 10. Briefly, ultrasonic instrument 10 includes a substantially cylindrical outer housing 12, preferably formed from molded housing half-sections, having an open distal end 14 and a closed proximal end 16. The housing 12 may be formed with a gripping member 17. The proximal end 16 of housing 12 is formed with a slot 18 dimensioned to slidably receive an actuation rod 20 which will be discussed in further detail below. A remotely located ultrasonic generator 22 is electrically connected to a transducer 23 via conventional means, such as a power cable 34. The transducer 23 is supported within the housing and engages a vibrator coupler 24 which extends longitudinally towards the distal end 14 of housing 12. A blade member 26 having a cutting edge 32 is provided at the distal end of the vibration coupler 24. The blade member 26 is fixedly connected to the vibration coupler 24 or alternately integral therewith, such that the cutting edge 32 defines a plane oriented at an acute fixed angle, preferably from about 30 degrees to about 70 degrees, with respect to the longitudinal axis of the instrument.

Ultrasonic generator 22 provides electrical energy having ultrasonic frequency to the transducer 23 to cause oscillation of the transducer 23 in a known manner. The transducer 23, which may be one of a variety of electromechanical types, e.g., electrodynamic, piezoelectric, magnetostrictive, is connected in end-to-end relation to the vibration coupler 24 to cause oscillation of the vibration coupler and corresponding oscillation of angled blade member 26.

Actuation rod 20 is movably supported within housing 12 and extends from the proximal end of housing 12, via slot 18, through the open distal end 14 of housing 12. Preferably, rod 20 is supported by brackets 36 which may be integrally formed with housing 12, although any conventional support structure which allows for linear movement of the actuation rod may be used. A proximal engagement surface 38 located externally of the housing 12 facilitates selective advancement of the actuation rod 20. Clamp 28 is connected to the distal end of the actuation rod 20 and includes clamp surface 30 which is substantially parallel to and faces cutting edge 32 of blade member 26. The clamp 28 is movable with respect to the blade member 26 from an open position to a closed position to capture tissue between the cutting edge 32 and the clamp surface 30. The clamp 28 may alternately be formed integral with the actuation rod 20 and may have a smooth texture although a knurled or ribbed surface may be provided to facilitate grasping of tissue or to enhance coagulation.

Figure 2A:
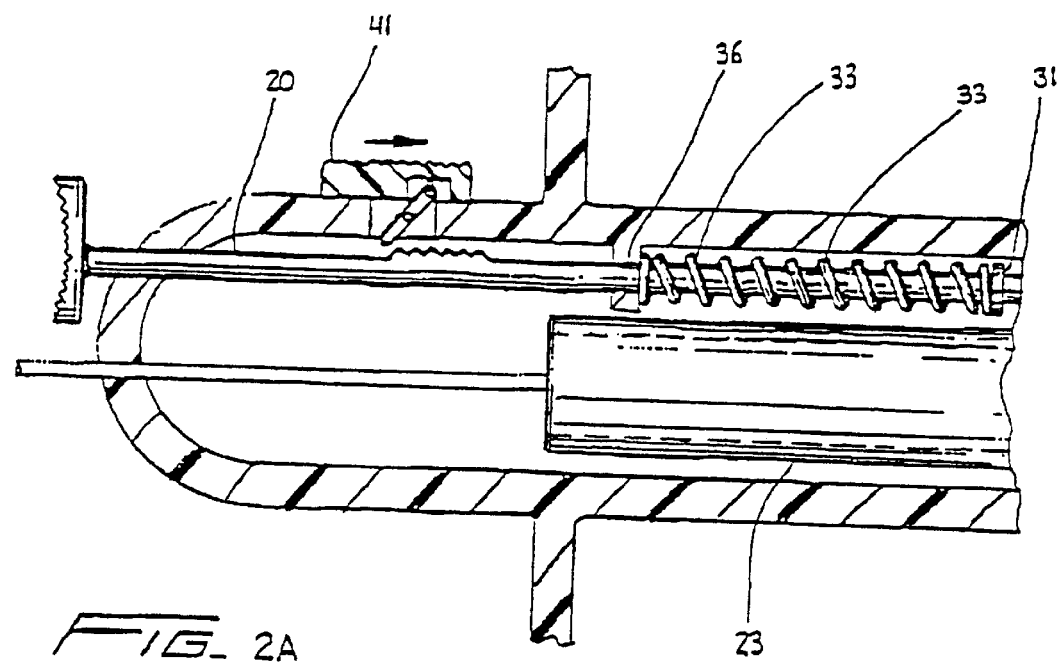
FIG. 2A is a side partial cross-sectional view of the proximal end of the ultrasonic instrument shown in FIG. 1 with the actuation rod biased to its distal-most position.

Referring to FIGS. 2A–2B, a biasing mechanism may be provided to bias the actuation rod 20 to a distal position and thus bias clamp 28 to the closed position. The biasing mechanism includes an annular ring 31 secured to or formed integrally with the is actuation rod 20 and a biasing spring 33. Biasing spring 33 is positioned about the actuation rod 20 between bracket 36 formed on housing 12 and annular ring 31 to continuously urge the actuation rod 20 distally. (See FIG. 2A.) A retaining member 35 is pivotally secured within a slot 37 formed in the housing and is pivotable into engagement with a rack 39 formed on the actuation rod 20. The retaining member 35 can be pivoted in the counterclockwise direction by moving slide member 41 proximally, as viewed in FIG. 2B, to selectively retain the clamp 28 at various locations between the open and closed positions. The slide member 41 may be moved distally to disengage retaining member 35 from rack 37, as illustrated in FIG. 2A, to clamp tissue 50 between the clamp surface 30 and the cutting edge 32.

In use, the ultrasonic instrument 10 is grasped about the proximal end of housing 12 and moved to position the cutting edge 32 adjacent tissue to be dissected and/or coagulated. The actuation rod 20 is retracted against the bias of spring 33 by pulling the engagement surface 38 of actuation rod 20 to retract clamp 28 away from blade 26 and provide access for tissue. In the open position, the clamp 28 is spaced from the blade member 26 a distance to permit easy tissue access. (See FIGS. 2C and 4.) When tissue 50 is positioned between clamp 28 and blade 26, engagement surface 38 is released to allow biasing spring 33 to move clamp 28 to the closed position and to capture tissue 50 therebetween. (See FIGS. 2D and 4A.) The actuation rod 20 may be retained in the retracted position while the instrument 10 is positioned about tissue by pivoting retaining member 35 counter-clockwise into engagement with rack 39 formed on actuation rod 20. (See FIG. 2B.) Clearly, other means to retain actuation rod 20 can be utilized. The ultrasonic generator 22 is energized to cause linear oscillation of the blade 26 with respect to the clamp 28 to effect dissection and/or coagulation of tissue 50. Alternately, the actuation rod 20 may be biased proximally to the open position so the clamp is biased to the open position. In this alternate embodiment, a retaining means can be utilized to retain the clamp in the closed position.

Figure 5:
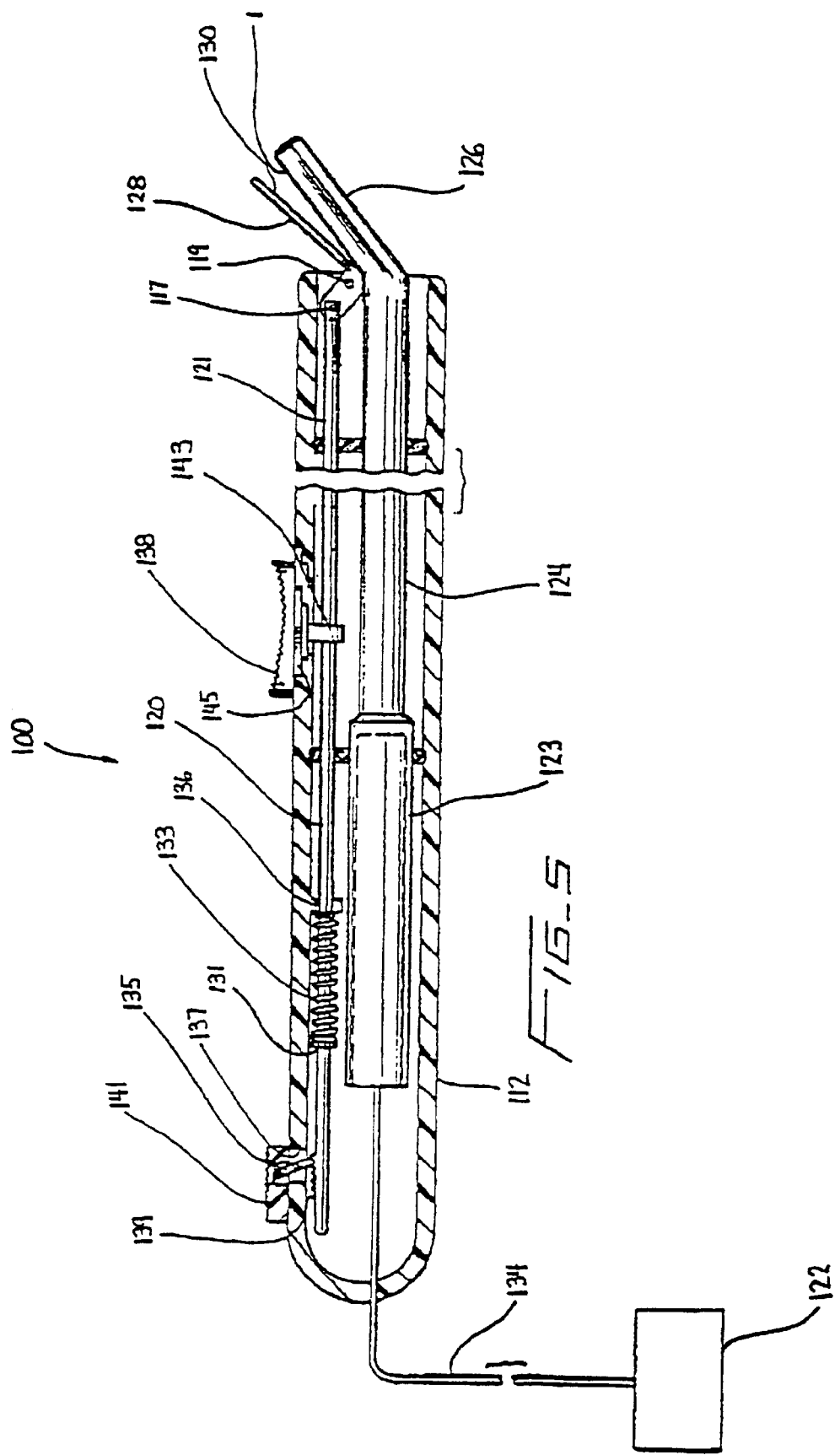
FIG. 5 is a side partial cross-sectional view of an alternate embodiment of the ultrasonic instrument.
Figure 6:
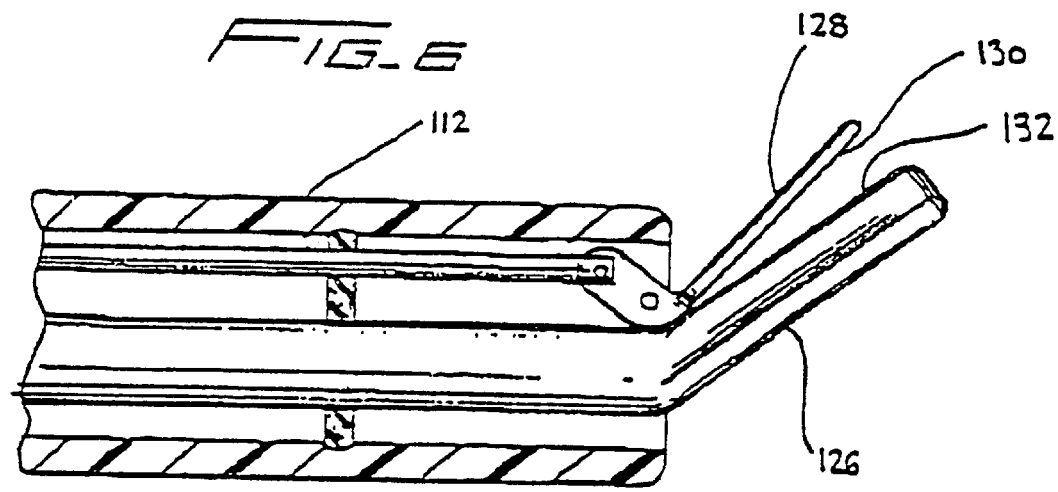
FIG. 6 is a side partial cross-sectional view of the blade member and clamp member shown in FIG. 5 with the clamp member in the open position.
Figure 6A:
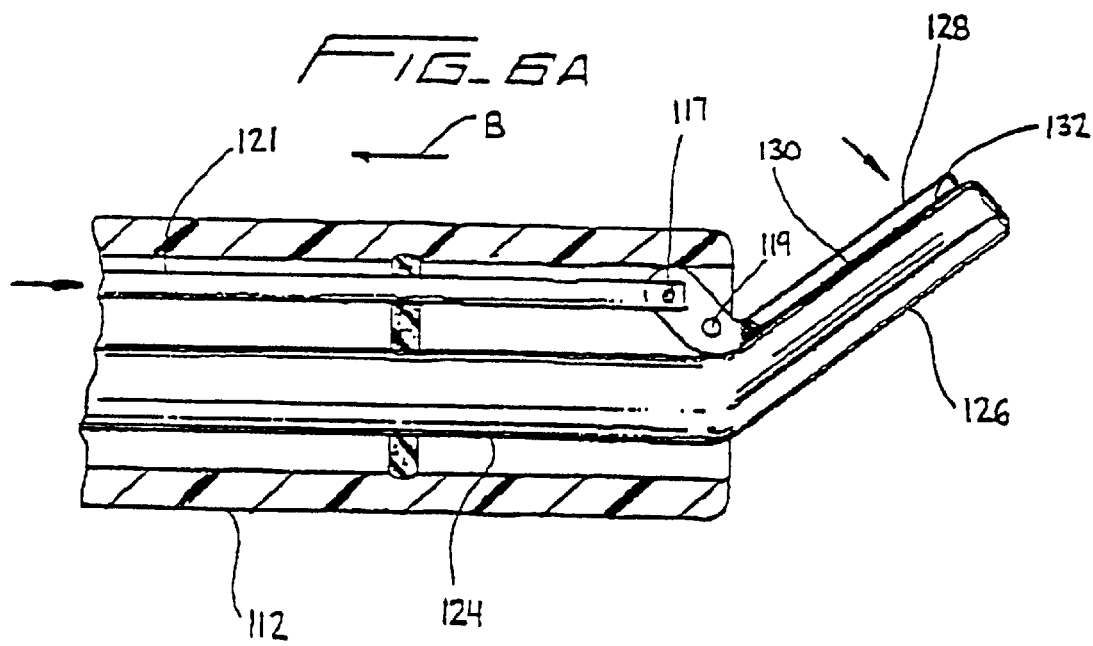
FIG. 6A is a partial side cross-sectional view of the blade member and the clamp member shown in FIG. 5 in the closed position.

FIGS. 5–6A illustrate a further embodiment of the presently disclosed ultrasonic dissector shown generally as 100. Ultrasonic dissector 100 is provided with a pivotable clamp 128. Briefly, ultrasonic dissector 100 includes a transducer 123 supported within a housing 112 and adapted to be connected to an ultrasonic generator 122 via power cable 134. The transducer 123 engages a vibration coupler 124 having a blade member 126 rigidly attached, or alternatively integral, to the distal end of the coupler 124 therewith.

A clamp 128 is pivotably mounted to the distal end of housing 112 about pivot member 119 such that clamp 128 extends through an open distal end 114 of housing 112. Actuation rod 120 is supported on brackets 136 for linear movement within housing 112. The distal end 121 of actuation rod 120 is connected to a proximal end of clamp 128 via pin 117 to translate linear advancement of the actuation rod 120 to clockwise rotation of clamp 128.

A thumb actuation member 138 is fixedly connected to actuation rod 120 by a link 143. The link 143 extends through slot 145 formed in housing 112 to facilitate linear advancement of the thumb actuation member 138 and corresponding linear advancement of the actuation rod 120. A biasing mechanism for biasing the actuation rod to a proximal position and a retaining mechanism to retain the actuation rod 120 in a distal position is shown in FIG. 5. Alternately, as discussed with respect to FIG. 2, the actuation rod 120 may be biased distally to maintain clamp member 128 in the closed position. In this alternate embodiment, a retaining member can be utilized to retain the clamp in the open position.

More specifically referring to FIGS. 5–6B, clamp member 128 of ultrasonic instrument 100 is biased to the open position by biasing spring 133, which engages annular ring 131 to urge actuation rod 120 proximally. After the instrument 100 is properly positioned about tissue, actuation rod 120 may be advanced distally against the bias of spring 133, via actuation member 138, to pivot the clamp member 128 into substantial alignment with blade member 126 and capture tissue between clamp surface 130 and cutting edge 132. (See FIG. 6A.) The retaining member 135 may be pivoted clockwise to retain the clamp member 128 and blade member 126 in the closed position. Clearly, other means to retain the clamp member 128 in the closed position can be utilized After tissue is captured between the clamp member and the blade member, the ultrasonic generator 122 may be actuated to effect dissection and/or coagulation of body tissue. As illustrated in FIG. 6A, the instrument may be moved proximally, during operation of the instrument, as indicated by arrow "B", to increase the force applied by the cutting edge 132 on body tissue 150.

It will be understood that various modifications may be made to the embodiments disclosed herein. For example, different handle assemblies may be provided on the proximal end of the instrument to improve gripping of the instrument, e.g., pistol grip. Also, the clamp member may be biased to the open or closed position. Therefore, the above description should not be construed as limiting, but merely as exemplifications of preferred embodiments. Those skilled in the art will envision other modifications within the scope and spirit of the claims appended thereto.

What is claimed is:

1. A surgical cutting instrument comprising:

a housing defining a longitudinal axis;

a vibration coupler positioned within the housing and having a proximal end positioned to engage an ultrasonic generator;

a tool member supported adjacent a distal end of the vibration coupler and having a cutting surface;

a clamp pivotally connected to the housing, the clamp being positioned adjacent the tool member and being movable from an open position spaced from the cutting surface to a closed position in close alignment with the cutting surface;

an actuation member operably connected to the clamp and being movable to move the clamp between the open and closed positions; and a retaining mechanism supported by the housing, the retaining mechanism being positioned and configured to selectively retain the clamp at a plurality of positions in relation to the cutting surface of the tool member.

2. A surgical cutting instrument according to claim 1, further including a biasing mechanism for urging the clamp toward the open position.

3. A surgical cutting instrument according to claim 2, wherein the retaining mechanism is positioned to selectively retain the clamp at multiple distinct positions between the open position and the closed position.

4. A surgical cutting instrument according to claim 3, wherein the actuation-member includes a rod.

5. A surgical cutting instrument according to claim 4, wherein the retaining mechanism includes a rack positioned on the actuation rod.

6. A surgical cutting instrument according to claim 5, wherein the retaining mechanism further includes a retaining member, the retaining member being movable into operable engagement with the rack to retain the clamp in multiple locations between the open and closed positions.

7. A surgical cutting instrument according to claim 1, wherein the cutting surface of the tool member defines an axis which extends radially outwardly of the longitudinal axis of the vibration coupler.

8. A surgical cutting instrument according to claim 7, wherein the cutting surface of the tool member is linear.

9. A surgical cutting instrument according to claim 8, wherein the cutting surface of the tool member and the longitudinal axis of the vibration coupler define a fixed obtuse angle.

10. A surgical instrument according to claim 1, wherein the cutting surface of the tool member is linear.

11. A surgical instrument according to claim 10, wherein the cutting surface of the tool member is continuous from a proximal end of the cutting surface to a distal end of the cutting surface.

12. An ultrasonic instrument comprising:

a cylindrical body defining a lumen and having a longitudinal axis;

a vibration coupler being positioned within the body and having a first end configured to be operably connected to an ultrasonic generator and a second end supporting a tool member;

a clamp member pivotally supported adjacent the tool member about a pivot axis, the clamp member being pivotable between an open position spaced from the tool member and a closed position in juxtaposed alignment with the tool member; and a retaining mechanism positioned to selectively retain the clamp member in multiple distinct positions between the open and closed positions.

13. An ultrasonic instrument according to claim 12, further including a biasing mechanism for urging the clamp member towards the open position.

14. An ultrasonic instrument according to claim 12, further including an actuation member including a rod.

15. An ultrasonic instrument according to claim 5, wherein the retaining mechanism includes a rack positioned on the actuation rod.

16. An ultrasonic instrument according to claim 15, wherein the retaining mechanism further includes a retaining member, the retaining member being movable into operable engagement with the rack to retain the clamp member at multiple locations between the open and closed positions.

17. An ultrasonic instrument according to claim 12, wherein the tool member defines an axis which extends radially outwardly of the longitudinal axis of the vibration coupler.

18. An ultrasonic instrument according to claim 17, wherein the tool member includes a linear cutting surface.

19. An ultrasonic instrument according to claim 8, wherein a cuffing surface of the tool member and the longitudinal axis of the vibration coupler define a fixed obtuse angle.

20. An ultrasonic instrument according to claim 18, wherein the linear cutting surface of the tool member is continuous from a proximal end of the cutting surface to a distal end of the cutting surface.

21. A surgical cutting instrument according to claim 1, wherein the clamp is pivotally connected to the housing at a location offset from the longitudinal axis of the housing.

22. An ultrasonic instrument according to claim 12, wherein the pivot axis is spaced radially of the longitudinal axis of the cylindrical body.

23. An ultrasonic instrument according to claim 18, wherein the linear cutting surface is positioned at an angle to the longitudinal axis of the housing.

* * * * *